United States Patent [19]
Becher et al.

[11] Patent Number: 6,143,320
[45] Date of Patent: Nov. 7, 2000

[54] METHOD FOR THE APPLICATION OF AN ACTIVE SUBSTANCE PATCH FOR CONTROLLING OR ALLEVIATING AN ADDICTION

[75] Inventors: Frank Becher, Koblenz; Werner Wessling, Rengsdorf, both of Germany

[73] Assignee: LTS Lohmann Therapie - Systeme GmbH, Germany

[21] Appl. No.: 09/173,804

[22] Filed: Oct. 16, 1998

[30] Foreign Application Priority Data

Oct. 18, 1997 [DE] Germany ............................ 197 46 191

[51] Int. Cl.⁷ ............................ A61F 13/00; A01N 43/42

[52] U.S. Cl. ............................ 424/449; 424/447; 514/282

[58] Field of Search ................................ 424/449, 447; 514/282

[56] References Cited

U.S. PATENT DOCUMENTS 5,026,556  6/1991  Drust et al. .............................. 424/449
5,968,547  10/1999  Reder et al. ............................. 424/449

*Primary Examiner*—Thurman K. Page
*Assistant Examiner*—Isis Ghali
*Attorney, Agent, or Firm*—James Klaniecki; Ann W. Speckman

[57] ABSTRACT

A method for the application of an active substance patch for controlling or alleviating an addiction such as drug addiction, addiction to pills or analgesia is characterized in that two or more active substance patches are applied simultaneously, sequentially or alternately within a given therapy plan under surveillance of the blood level of the active substance in a way that allows the achievement of an active substance blood level which is high enough for a successful suppression of the addiction and remains constantly effective throughout a useful period of administration.

6 Claims, No Drawings

METHOD FOR THE APPLICATION OF AN ACTIVE SUBSTANCE PATCH FOR CONTROLLING OR ALLEVIATING AN ADDICTION

The invention relates to a method for the application of an active substance patch for controlling or alleviating an addiction such as drug addiction, addiction to pills or analgesia. Furthermore, the invention relates to a utilization of this method.

Transdermal forms of administration provide important advantages for the treatment of addictions such as drug addiction, addiction to pills or analgesia:

1. The improper extraction of active substances and, consequently, "dealing" of the pure active substance is extremely difficult and expensive and thus normally impossible and pointless for the addict.
2. The absorption of the medicinal agent can easily be monitored by a surveillance of the blood level.
3. The application can be interrupted at any given time, for example if an addict additionally consumes the addictive drug during the treatment although not allowed to do so.
4. The transdermal application is suited for achieving a constant blood level of the active substance.
5. The whereabouts of the medication can be monitored, for example by means of exchange systems.

However, the fact that the higher blood levels necessary for the successful control or alleviation of an addiction are not obtainable by means of the forms of administration of transdermal therapeutic systems (TTS) available on the market, e.g. TTS containing buprenorphine, poses a problem. dosage by means of an increase in the size of the patches is also unacceptable due to the resulting lower level of wear comfort. In addition, the necessary dosage with a patch by means of an increase in its size would not be able to achieve a constant blood level because the pharmacokinetics of such a patch can not simply be adjusted to obtain a constant higher blood level for the desired period of time, e.g. seven days and longer.

It is thus the object of the invention to provide a method for the application of a TTS containing an active substance for the purpose of controlling or alleviating an addiction such as drug addiction or addiction to pills, achieving a blood level of e.g. buprenorphine base high enough and constant enough for successful therapy throughout a useful duration of treatment—e.g. seven days and longer.

To achieve this object, the invention proposes, on the basis of a method of the kind mentioned in the introductory part of claim 1, the simultaneous, sequential or alternating application of two or more active substance patches within a given therapy plan and under supervision of the blood level of the active substance in a way that allows the achievement of an active substance blood level which is high enough for a successful suppression of the addiction and remains constantly effective throughout a useful period of administration.

The simultaneous, sequential or alternating application of two or more active substance TTS should meet with sufficient acceptance in view of the intended indication. In addition, frequent medical examinations of drug addicts, i.e. at least every three or four days, are advisable in any case to detect any additional consumption of addictive drugs which could be harmful to the treatment, as well as other disturbances of health.

One embodiment provides that a useful period of administration with a given blood level of the active substance is achieved by means of the application of two or more patches in sequence over a period of at least seven days. Thus, optimum wear comfort is guaranteed and it is possible, provided reasonable conduct on the part of the addict, to achieve a gradual decrease of the addictive potential over a longer period of time and consequently a gradual reduction of the effect of the addiction.

Another embodiment further provides for the initial application of one patch with a defined period of application of several days and an accordingly short half-life of the active substance flux. A second patch is applied before the half-life of the first is reached, e.g. after three days, and especially before the blood level begins to decline, resulting in an overlap with the period of effect of the first patch.

An especially advantageous embodiment of the method for the application of a patch containing the active substance buprenorphine provides for the initial application of at least two TTS. A third patch is applied before the half-life of the first patches is reached, and a still further TTS is applied several days afterward, especially in the case of depletion of the first patches but in any case before a discernible decline of the prescribed blood level occurs, and so forth. Thus, new patches are applied in sequence, and the respective oldest patches are also removed from the skin in sequence upon depletion.

A utilization of the method according to this invention is intended to achieve a therapeutic effect over a duration of several days by means of TTS which, if used singly, could not achieve the dosage rate and length of dosage necessary for a successful controlling of the addiction.

The following treatment is an example of an application according to this invention:

A TTS with a defined length of application of seven days is applied together with a second TTS of the same kind. After three days—i.e. before the blood level values begin to decrease—a third "fresh" TTS is applied, guaranteeing a constant blood level. Seven days after the application of the first patch, a fourth patch can be applied. After another three or four days, a fifth can be applied, and so on.

The invention is effective, it meets an urgent demand for addiction control by means of therapeutic measures already available as such, and it presents a safe way of reducing the danger of addictions without the necessity of lengthy and expensive new research. Thus, the invention presents an ideal means of achieving the object as mentioned above.

What is claimed is:

1. A method of controlling or alleviating addiction or of treating pain in a human patient by applying at least two transdermal therapeutic systems containing a therapeutically effective active substance in a temporally overlapping manner onto the skin of said human patient, wherein initially at least one transdermal therapeutic system containing said active substance is applied for a defined period of several days, and thereafter, before the half-life of the flux of the active substance of the first applied one or more transdermal therapeutic system(s) is reached, another transdermal therapeutic system containing said active substance is applied onto the skin of said human patient.

2. The method according to claim 1, wherein said transdermal therapeutic systems are applied within a given therapy plan and under supervision of the blood level of said active substance.

3. The method according of claim 1, wherein another transdermal therapeutic system containing the active substance is applied, before the blood level of the active substance begins to decline.

4. The method according to claim 1, wherein another transdermal therapeutic system containing the active substance is applied three days after the first application of one or more transdermal therapeutic system(s).

5. The method of claim 1, wherein the procedure of temporally overlapping application of transdermal therapeutic systems is continued over a period of at least seven days.

6. The method according to any claims 1 to 5, wherein the active substance is buprenorphine.

* * * * *